(12) United States Patent
Schuele

(10) Patent No.: US 9,788,900 B2
(45) Date of Patent: Oct. 17, 2017

(54) SURGICAL INSTRUMENT POSITIONING SYSTEM AND METHOD

(71) Applicant: pro med instruments GmbH, Freiburg im Breisgau (DE)

(72) Inventor: Matthias E. Schuele, Freiburg (DE)

(73) Assignee: pro med instruments GmbH, Freiburg im Breisgau (DE)

(*) Notice: Subject to any disclaimer, the term of this patent is extended or adjusted under 35 U.S.C. 154(b) by 221 days.

(21) Appl. No.: 14/554,101

(22) Filed: Nov. 26, 2014

(65) Prior Publication Data

US 2015/0148819 A1 May 28, 2015

Related U.S. Application Data

(60) Provisional application No. 61/908,940, filed on Nov. 26, 2013.

(51) Int. Cl.
| | |
|---|---|
| *A61B 19/00* | (2006.01) |
| *A61B 90/11* | (2016.01) |
| *A61B 90/10* | (2016.01) |
| *A61B 90/14* | (2016.01) |

(52) U.S. Cl.
CPC .......... *A61B 19/201* (2013.01); *A61B 90/11* (2016.02); *A61B 90/14* (2016.02); *A61B 2090/103* (2016.02)

(58) Field of Classification Search
USPC ........................................................ 606/130
See application file for complete search history.

(56) References Cited

U.S. PATENT DOCUMENTS

| | | |
|---|---|---|
| 4,750,487 A | 6/1988 | Zanetti |
| 8,016,835 B2 | 9/2011 | Birkmeyer et al. |
| 2006/0052689 A1 | 3/2006 | Scouten et al. |
| 2007/0055291 A1* | 3/2007 | Birkmeyer ............. A61B 90/13 606/130 |
| 2013/0081636 A1 | 4/2013 | Schuele |

FOREIGN PATENT DOCUMENTS

WO  2009/042130 A2  4/2009

OTHER PUBLICATIONS

International Search Report and Written Opinion dated Jun. 25, 2015 for Application No. PCT/IB2014/003183.

* cited by examiner

*Primary Examiner* — Nicole F Johnson
(74) *Attorney, Agent, or Firm* — Frost Brown Todd LLC

(57) ABSTRACT

A surgical instrument positioning system includes articulating arms for coarse adjustment and a micro manipulator connectable to the articulating arms for fine adjustment. The micro manipulator selectively holds the surgical instrument and is operable to adjust the position of the surgical instrument. The micro manipulator includes two adjustment assemblies for providing linear adjustment and two adjustment assemblies for providing rotational adjustment. Features of the system also provide for control of the amount of free movement or play within the micro manipulator. Also a stop feature works in conjunction with the adjustment assemblies to maintain the tip of the instrument at an intersection of the two rotational axes facilitating rotational adjustment of the micro manipulator without linear displacement of the instrument tip.

15 Claims, 16 Drawing Sheets

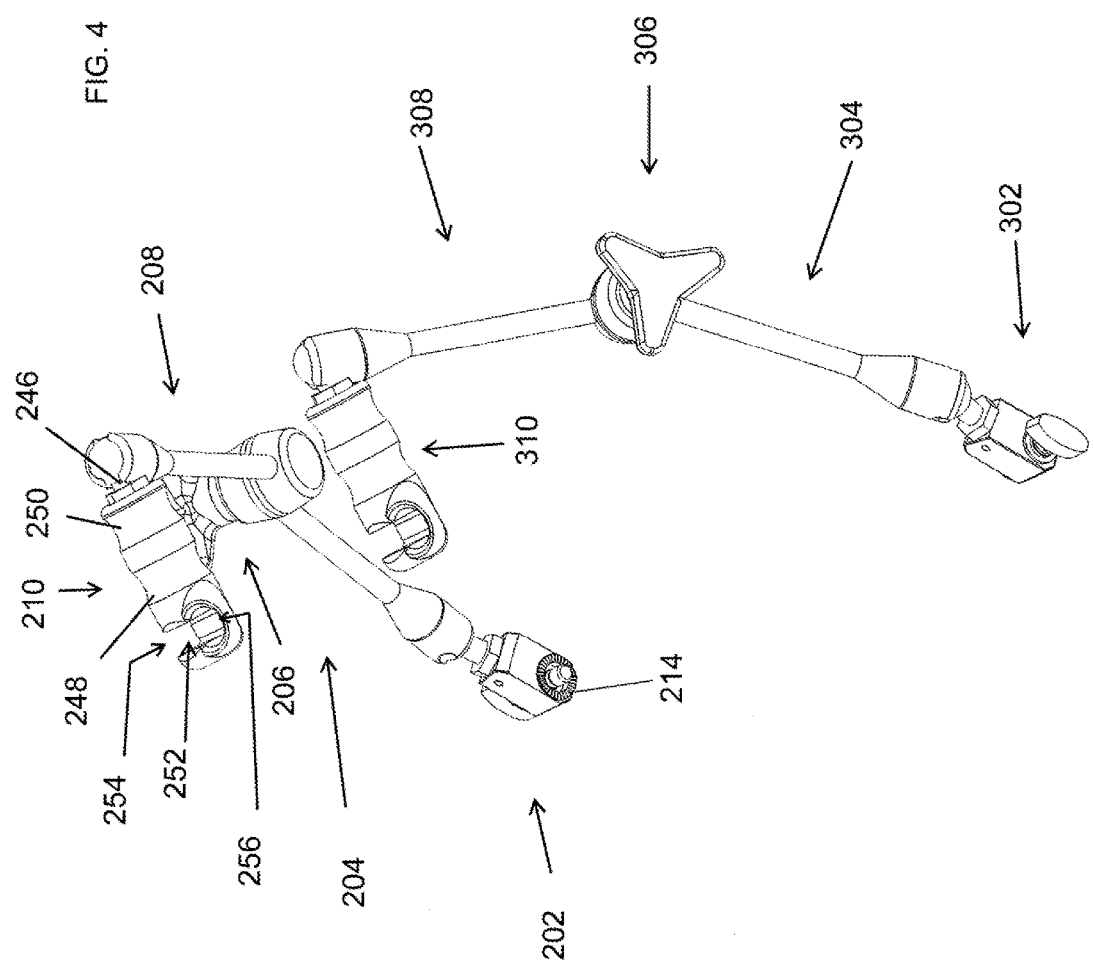

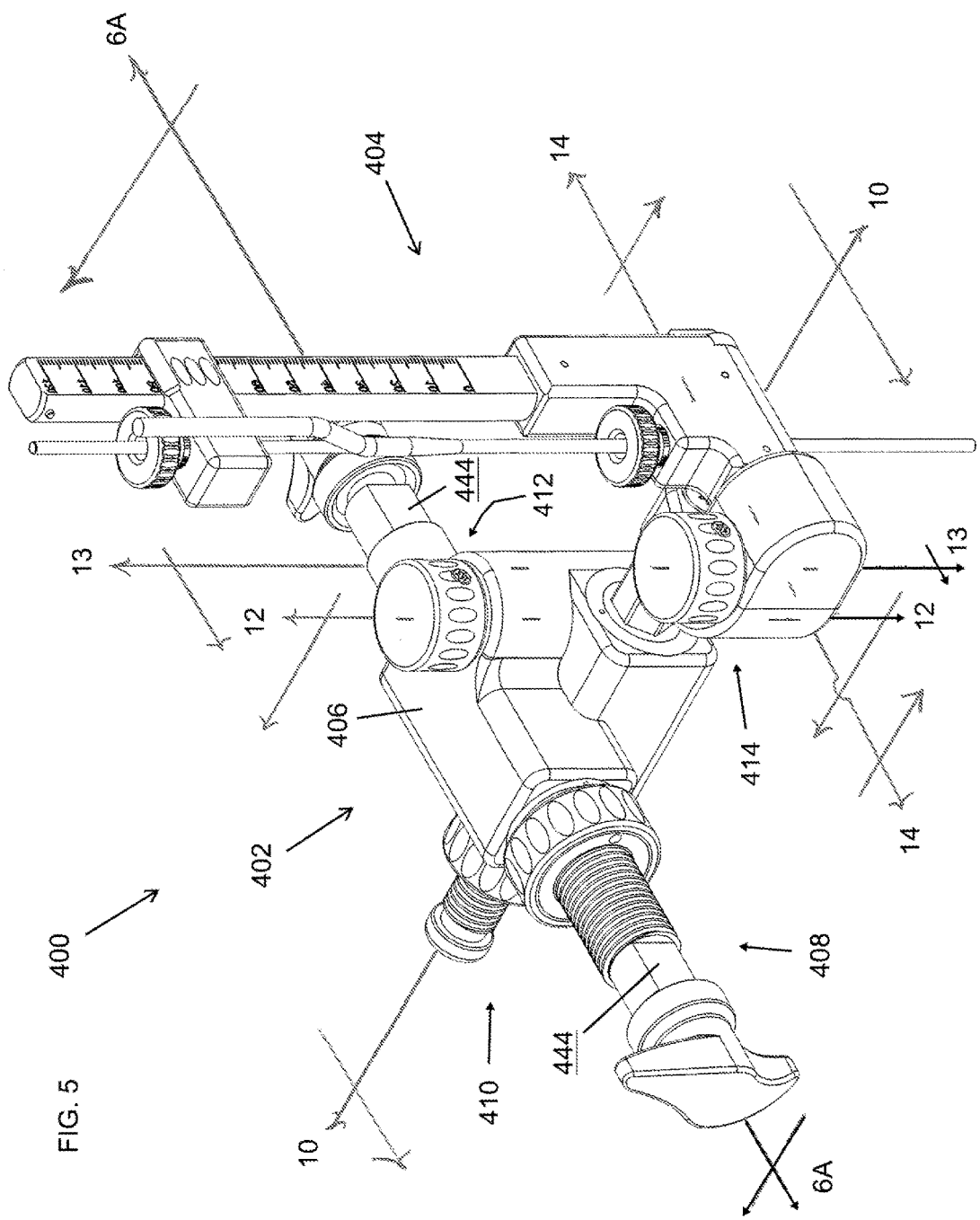

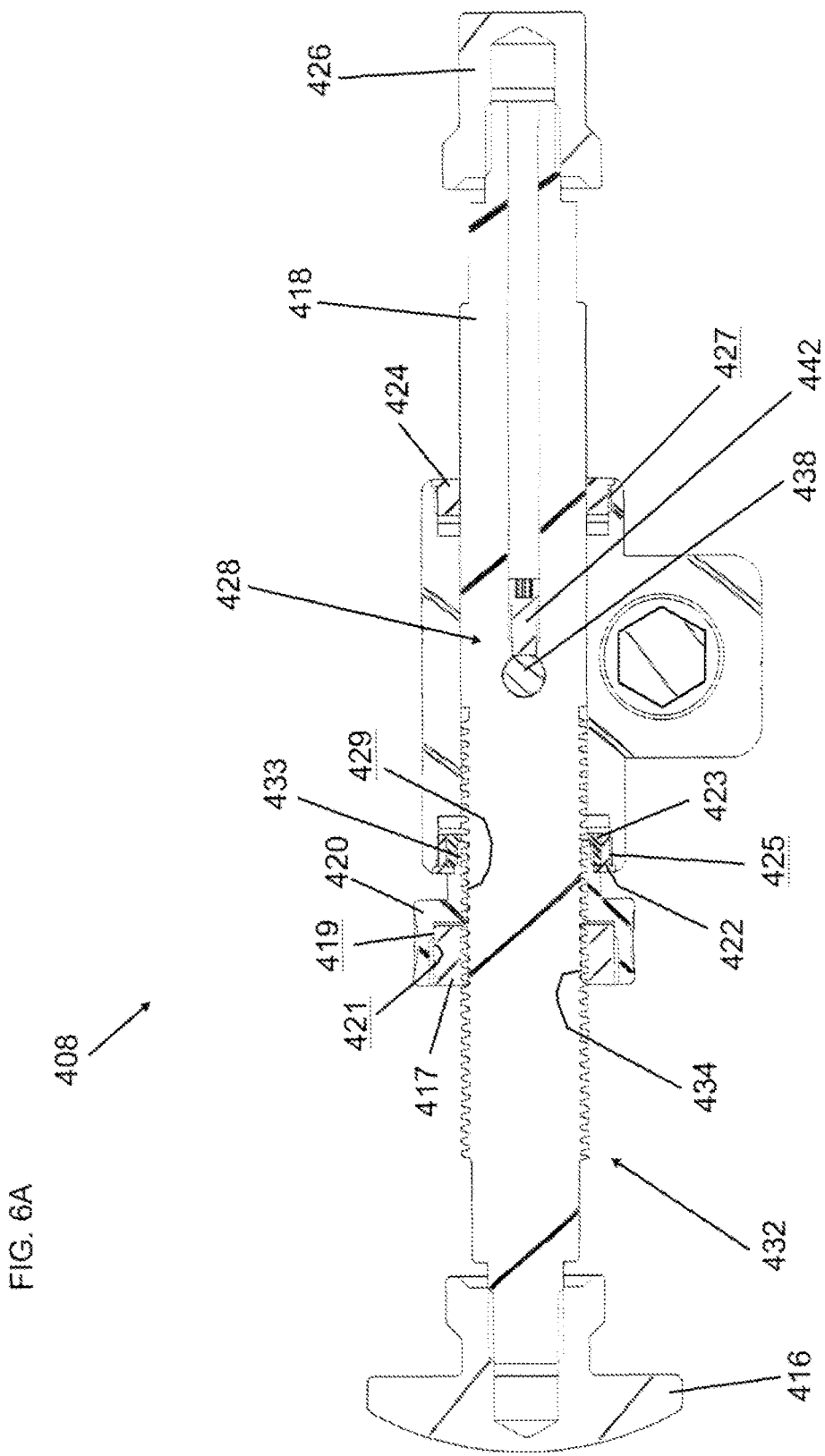

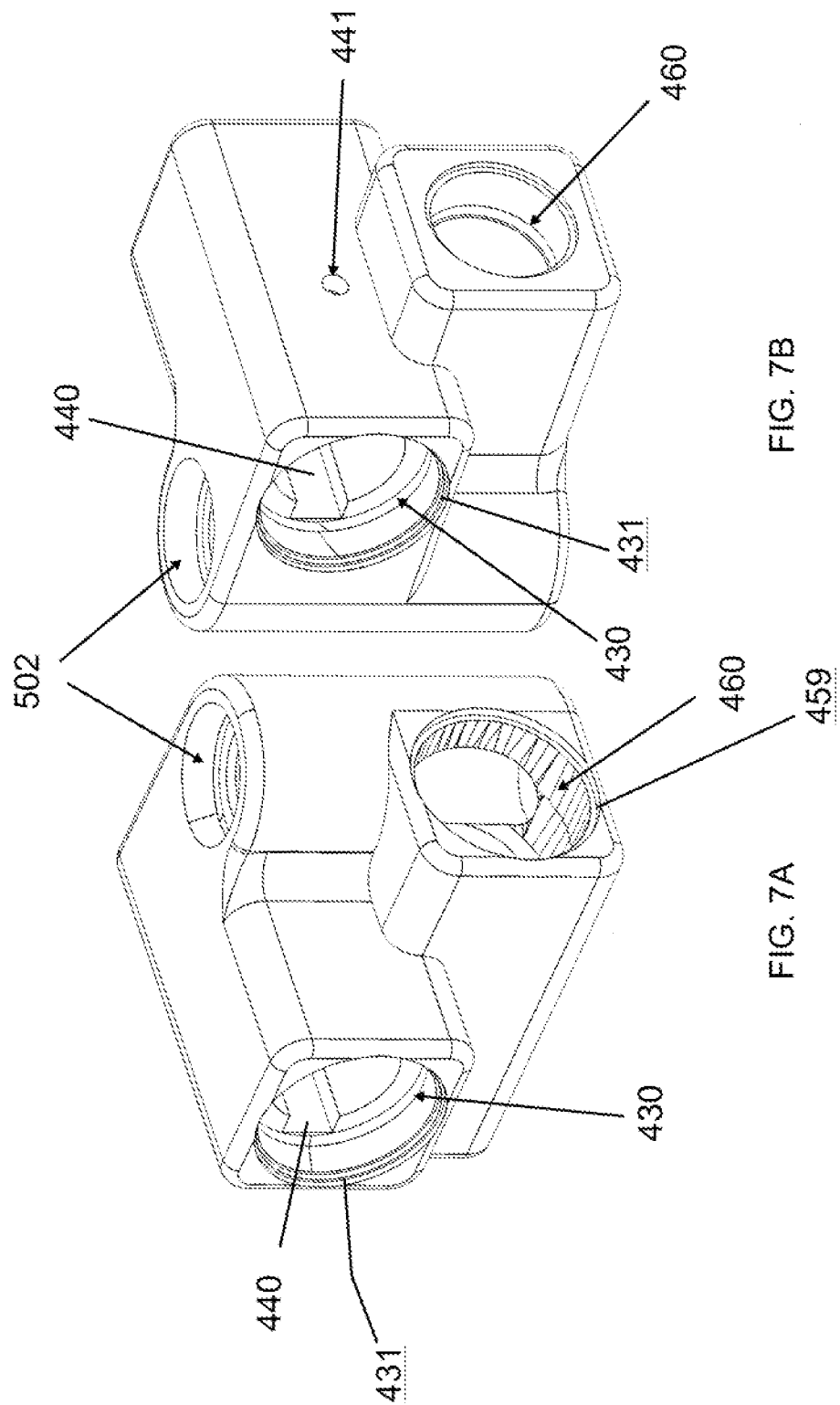

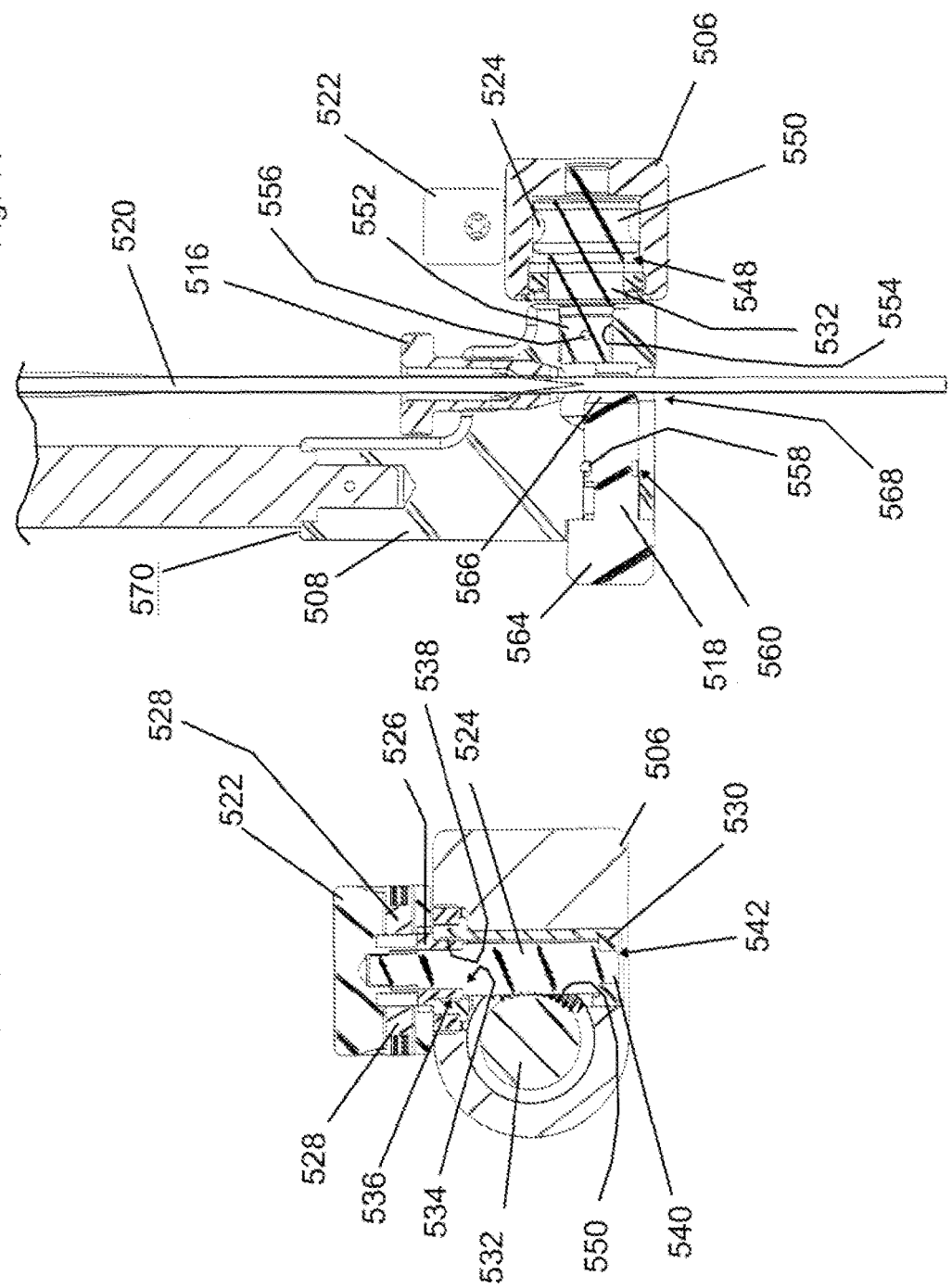

SURGICAL INSTRUMENT POSITIONING SYSTEM AND METHOD

PRIORITY

This application claims priority to U.S. Provisional Patent Application 61/908,940, filed Nov. 26, 2013, entitled "Surgical Instrument Positioning System and Method," the disclosure of which is incorporated by reference herein.

BACKGROUND

The present disclosure relates to a surgical instrument positioning system and method that uses a surgical device that can be used with navigation and imaging techniques, software and systems to conduct guided medical procedures. In some instances, such systems and methods can be used with or without image guided software applications.

While a variety of surgical systems and methods have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements.

FIG. 4 depicts a perspective view of the system as shown in FIG. 3, shown without the micro manipulator.

FIG. 5 depicts a perspective view of the micro manipulator as shown in FIG. 1.

FIG. 6A depicts cross section view taken along line 6A-6A shown in FIG. 5.

FIGS. 7A and 7B depict perspective views of an exemplary body used with the micro manipulator.

FIG. 13 depicts a partial cross section view taken along line 13-13 shown in FIG. 5.

FIG. 14 depicts a partial cross section view taken along line 14-14 shown in FIG. 5.

Figure 1:
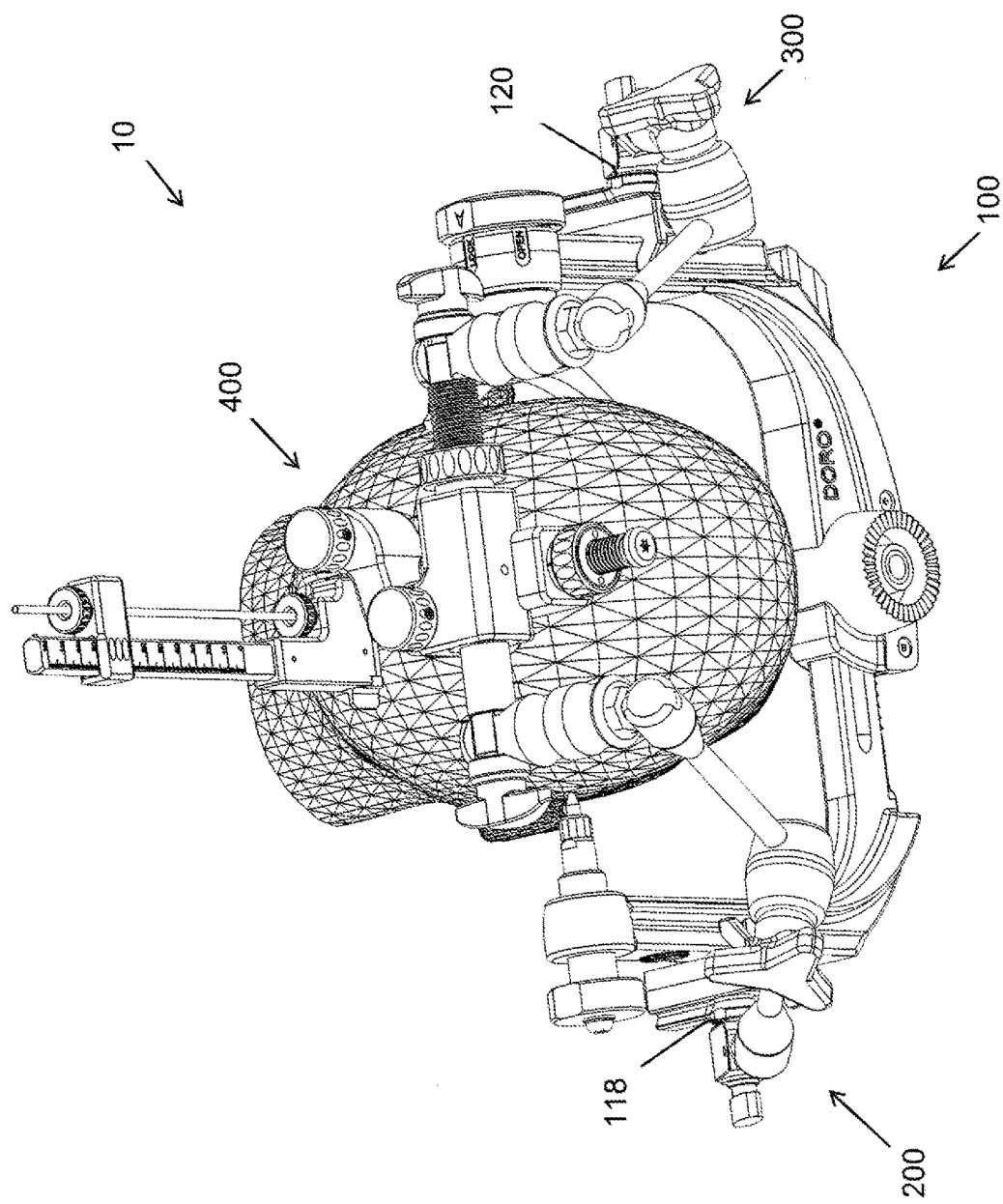
FIG. 1 depicts a perspective view of an exemplary surgical system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description. As will be realized, the invention is capable of other different and obvious aspects, all without departing from the invention. Accordingly, the drawings and descriptions should be regarded as illustrative in nature and not restrictive.

Figure 2:
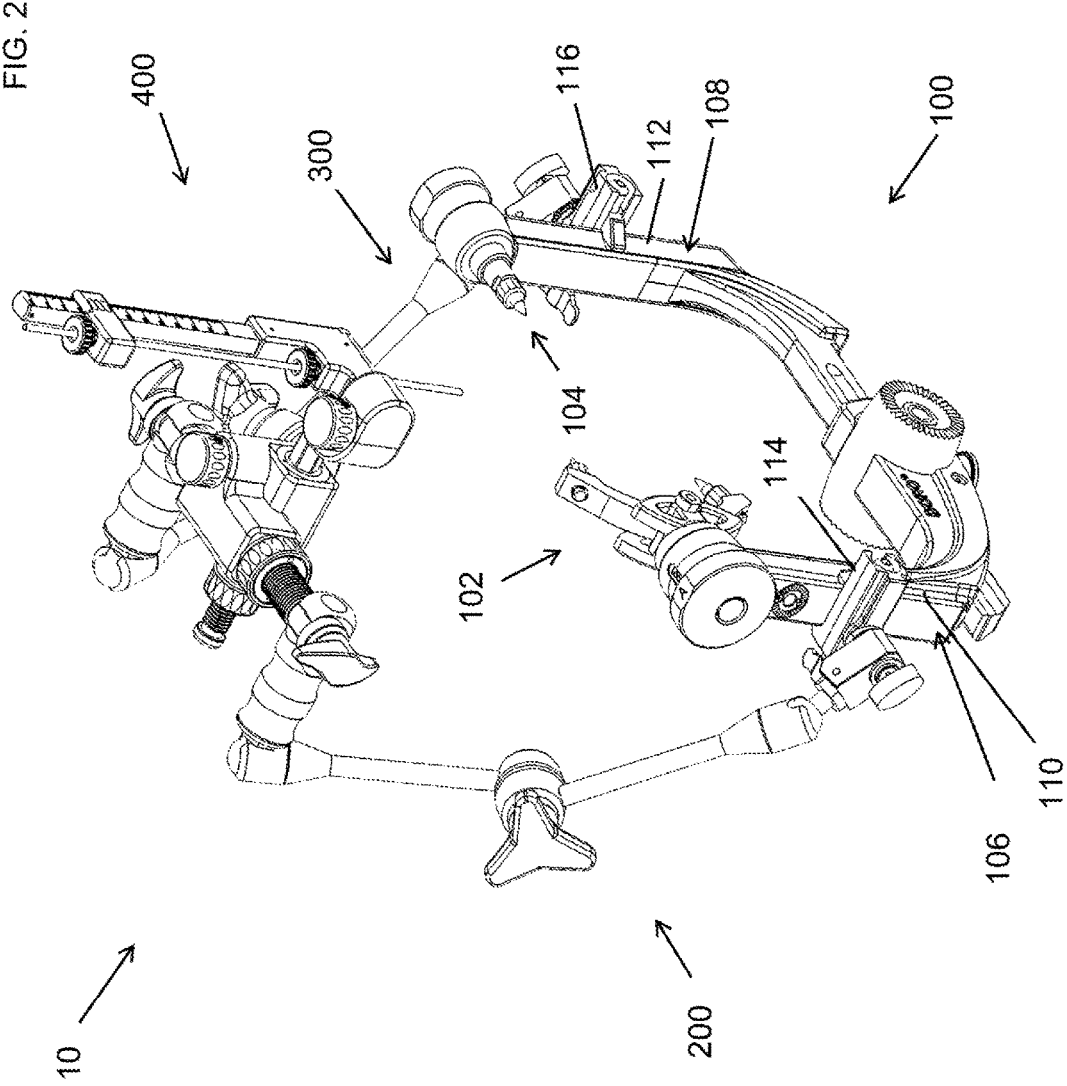
FIG. 2 depicts a perspective view of the system of FIG. 1, shown without the exemplary patient head.

FIG. 1 illustrates an exemplary surgical system (10) used in an exemplary surgical procedure involving the brain of a patient. Surgical system (10) comprises head fixation device (100) in the form of a skull clamp, first and second articulated arms (200, 300), and micro manipulator (400). FIG. 2 illustrates surgical system (10) shown without the exemplary patient head.

Exemplary Head Fixation Device

Head fixation device (100) is illustrated as a skull clamp with head fixation assemblies (102, 104) configured with skull pins for engaging the head of a patient. Head fixation device or skull clamp (100) comprises upright portions (106, 108) with rails (110, 112) that are configured to receive clamps (114, 116). An exemplary skull clamp (100) using clamps (114, 116) is shown and described in U.S. patent application US 2013/0081636, published Apr. 4, 2013, entitled HEAD FIXATION DEVICE AND APPARATUS FOR SECURING COMPONENTS THERETO, the disclosure of which is incorporated by reference herein. Clamps (114, 116) are configured with starburst features (118, 120) that, in the illustrated version, connect with first and second articulated arms (200, 300) respectively.

Exemplary Articulated Arms

Referring now to first and second articulated arms (200, 300), second articulated arm (300) has the same construction as first articulated arm (200). Therefore the description that follows of first articulated arm (200) applies equally to second articulated arm (300) with second articulated arm (300) having all the same components as first articulated arm (200). For ease of showing and describing first and second articulated arms (200, 300), those reference numbers of the 300 series correspond with those reference numbers of the 200 series. In other words, exemplary component (304) of second articulated arm (300) is the same in structure and function as exemplary component (204) of first articulated arm (200) and so forth as will be apparent to those of ordinary skill in the art based on the further description below and figures.

Figure 3:
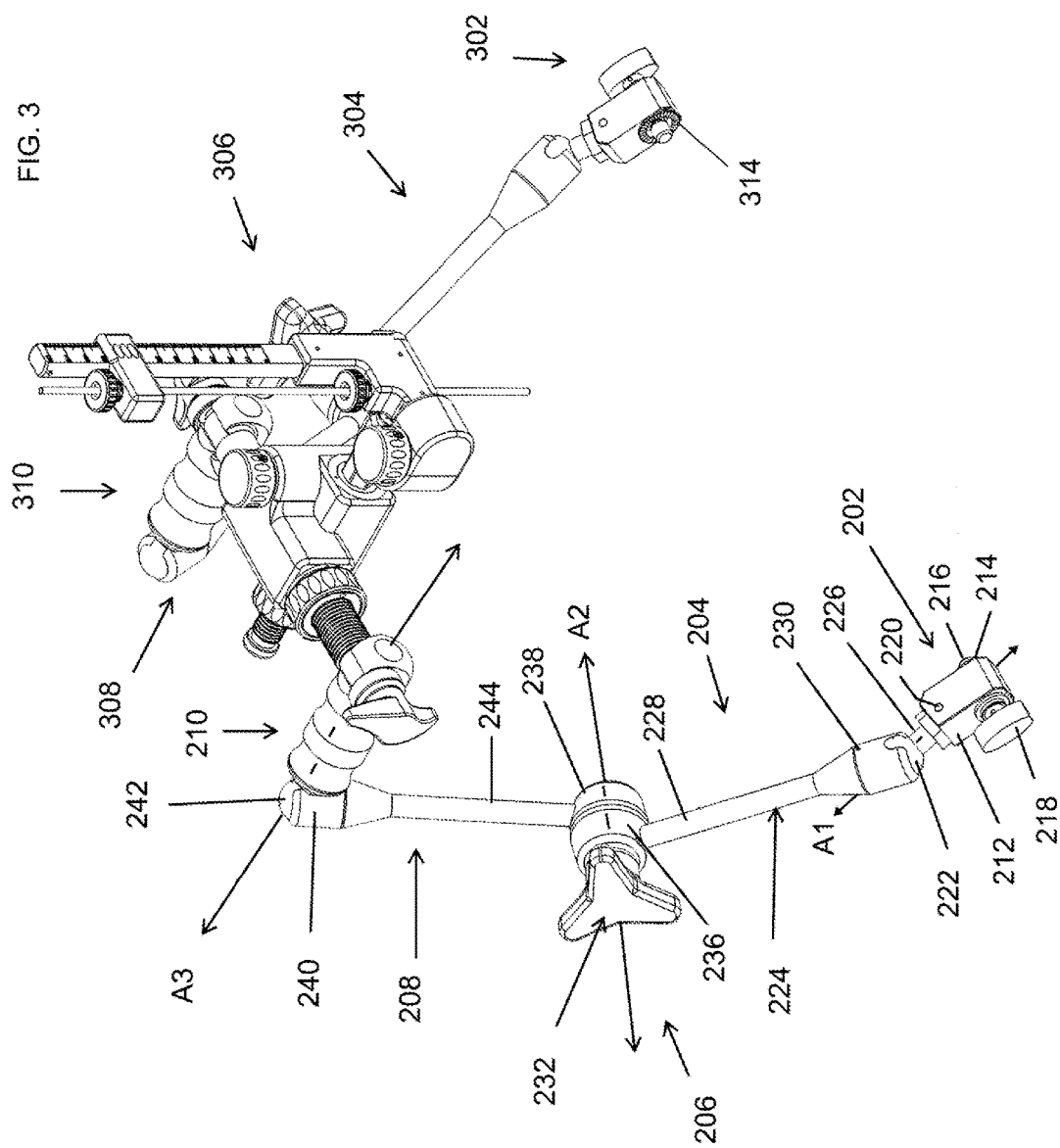
FIG. 3 depicts a perspective view of the system as shown in FIG. 2, shown without the head fixation device.

FIG. 3 illustrates portions of surgical system (10) where head fixation device (100), and the patient head are not shown to better illustrate first and second articulated arms (200, 300) and micro manipulator (400). FIG. 4 illustrates a similar view from a different angle but without micro manipulator (400). First articulated arm (200) comprises adapter (202), lower arm portion (204), locking member (206), upper arm portion (208), and positioning handle (210).

Adapter (202) comprises body (212), starburst feature (214), threaded rod (216), actuator (218) in the form of a knob. Body (212) comprises a bore through which threaded rod (216) extends. On one side of body (212) threaded rod (216) has an exposed threaded region for engaging a corresponding threaded bore of clamp (114) at the location of starburst feature (118). On the other side of body (212) threaded rod (216) connects with actuator (218). The connection of threaded rod (216) with actuator (218) is such that as actuator (218) is rotated, threaded rod (216) has a corresponding rotation. Body (212) also comprises a threaded bore that is configured to receive a threaded rod portion of lower arm portion (204). Body (212) includes a bore for receiving pin (220) that connects with the threaded rod portion of lower arm portion (204) as described in greater detail below. Starburst feature (214) of adapter (202) is configured to selectively engage with starburst feature (118) of clamp (114). To secure adapter (202), and hence first articulated arm (200), with clamp (114), threaded rod (216) threadably engages with the threaded bore of clamp (114). This threaded connection is tightened by rotating actuator (218) until starburst feature (118) and starburst feature (214) are engaged.

Lower arm portion (204) comprises sphere (222) and rod (224). Sphere (222) includes threaded rod (226) projecting from one end of sphere (222). Threaded rod (226) threadably engages a threaded bore within body (212) of adapter (202) as described above. Pin (220) secures sphere (222) with adapter (202). Rod (224) comprises elongated portion (228) and connecting member (230). Connecting member (230) is configured to receive sphere (222) in a fashion creating an adjustable ball joint that can be selectively locked in a desired position using locking member (206) as described further below. In this configuration, the joint between connecting member (230) and sphere (222) provides adjustment by allowing lower arm portion (204) to pivot in any direction about an axis (A1) defined by threaded rod (226). Elongated portion (228) extends and adjustably connects with locking member (206).

Locking member (206) comprises actuator (232) in the form of a knob, and body (234). Body (234) includes first portion (236) to which elongated portion (228) of lower arm portion (204) connects. Body (234) further includes second portion (238) to which upper arm portion (208) connects. First portion (236) and second portion (238) are rotatably adjustable with respect to one another about an axis (A2). This rotatable adjustment of first portion (236) and second portion (238) allow lower arm portion (204) and upper arm portion (208) to adjust rotatably about axis (A2) as well. Actuator (232) is configured to be rotatable such that rotation of actuator (232) selectively locks first portion (236) of body (234) with respect to second portion (238) of body (234) once lower arm portion (204) and upper arm portion (208) have been rotated into a desire position. Actuator (232), via the same rotatable action, selectively locks connecting member (230) relative to sphere (222). Even further, actuator (232), via the same rotatable action, selectively locks connecting member (240) of upper arm portion (208) with sphere (242) of upper arm portion (208) in a similar manner. Similar to lower arm portion (204), connecting member (240) of upper arm portion (208) connects with elongated portion (244) of upper arm portion (208). Certain exemplary articulated arms that provide the selective adjustment and locking features and capability the same or similar to articulated arms (200, 300) are available from GEOMED Medizintechnik GmbH & Co. KG under the product name ASSISTO Arm Systems, and from Baitella AG under its line of Fisso products. In view of the teachings herein, such commercially available articulated arms may be modified or adapted to work with the other components of surgical system (10) described herein.

Sphere (242) of upper arm portion (208) comprises a threaded rod (246) similar to threaded rod (226) of sphere (222). Threaded rod (246) threadably connects with a threaded bore (not shown) of positioning handle (210) such that sphere (242) is securely connected with positioning handle (210). Connecting member (240) is configured to receive sphere (242) in a fashion creating an adjustable ball joint that can be selectively locked in a desired position using locking member (206) as described above. In this configuration, the joint between connecting member (240) and sphere (242) provides adjustment by allowing upper arm portion (208) to pivot in any direction about an axis (A3) defined by threaded rod (246) of sphere (242).

Positioning handle (210) comprises grooves (248, 250) that serve as grip portions for a user's hands and/or fingers. Positioning member (210) also comprises slot (252) configured to receive a portion of micro manipulator (400). In the illustrated version, slot (252) has a U-shape but in other versions slot (252) can have other shapes. Slot (252) extends laterally through positioning handle (210) such that positioning handle (210) comprises first and second openings (254, 256) on each side of positioning handle (210). In the present example, openings (254, 256) are slightly recessed relative to the outermost surface of positioning handle (210). This recessed configuration provides space for components of micro manipulator (400) to contact positioning handle (210) and thereby secure micro manipulator (400) with positioning handle (210) as will be described further below.

Exemplary Micro Manipulator

Figure 8:
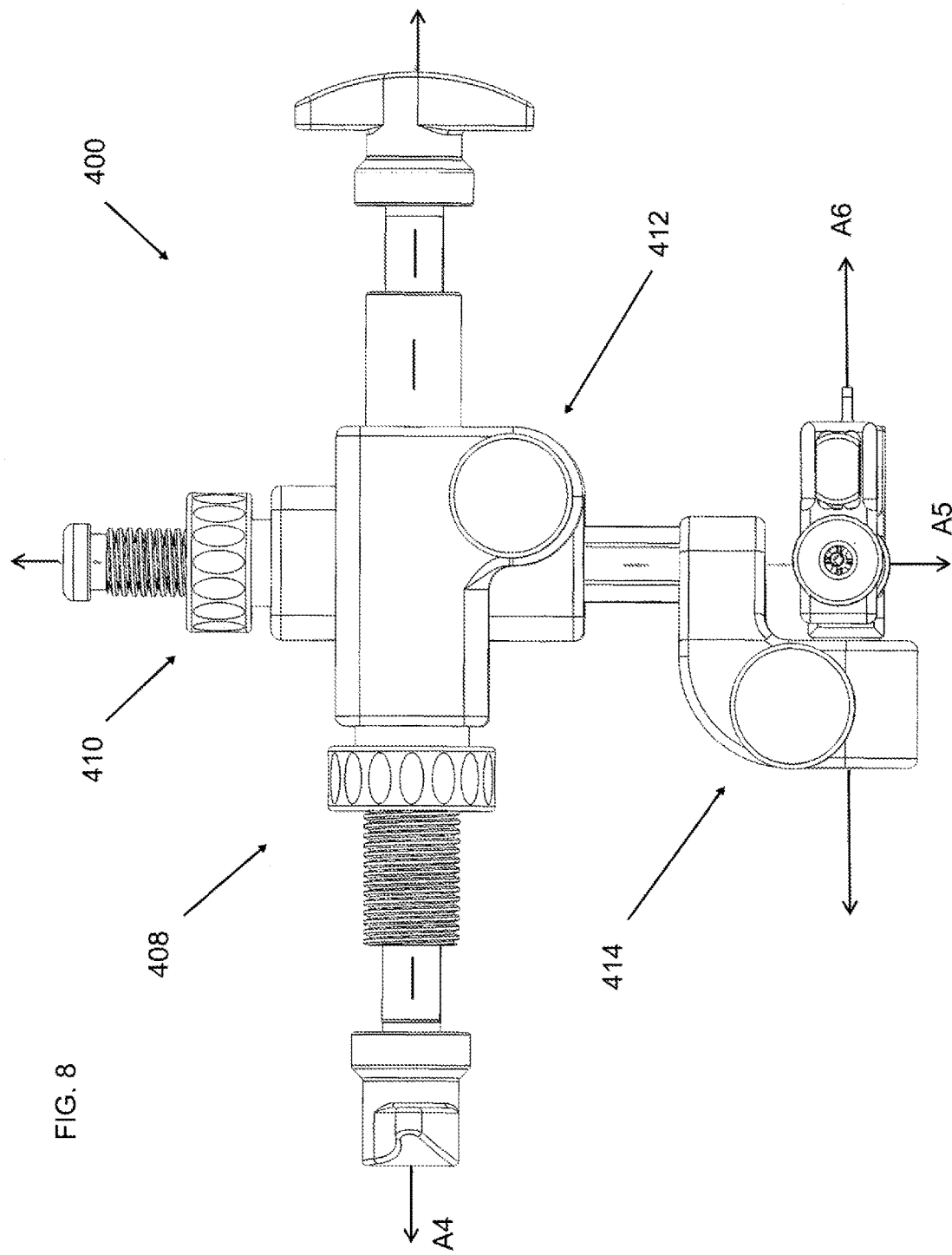
FIG. 8 depicts a top view of the micro manipulator as shown in FIG. 5, shown in a first adjustable position to show linear adjustments.
Figure 9:
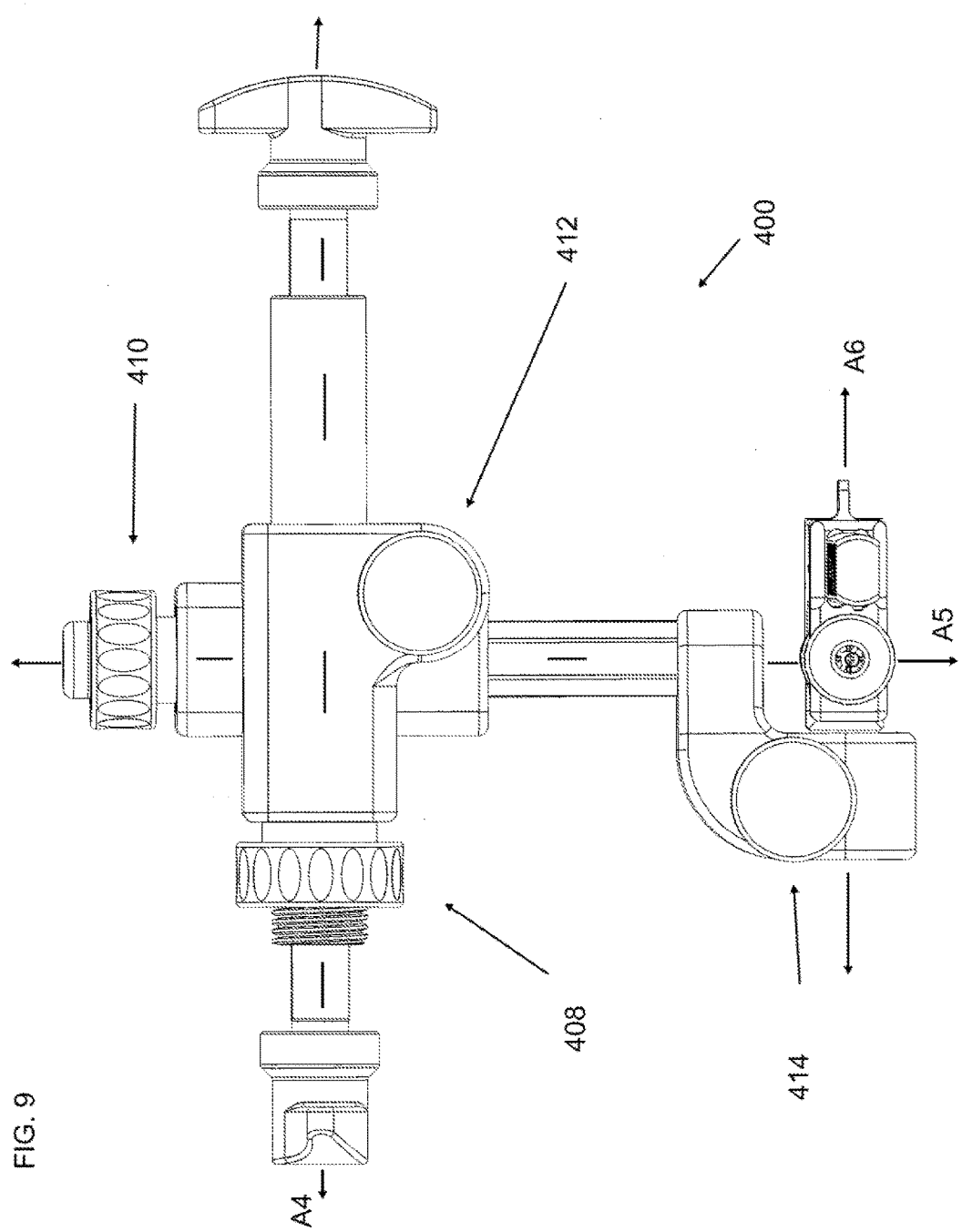
FIG. 9 depicts a top view of the micro manipulator as shown in FIG. 5, shown in a second adjustable position to show linear adjustments.
Figure 12:
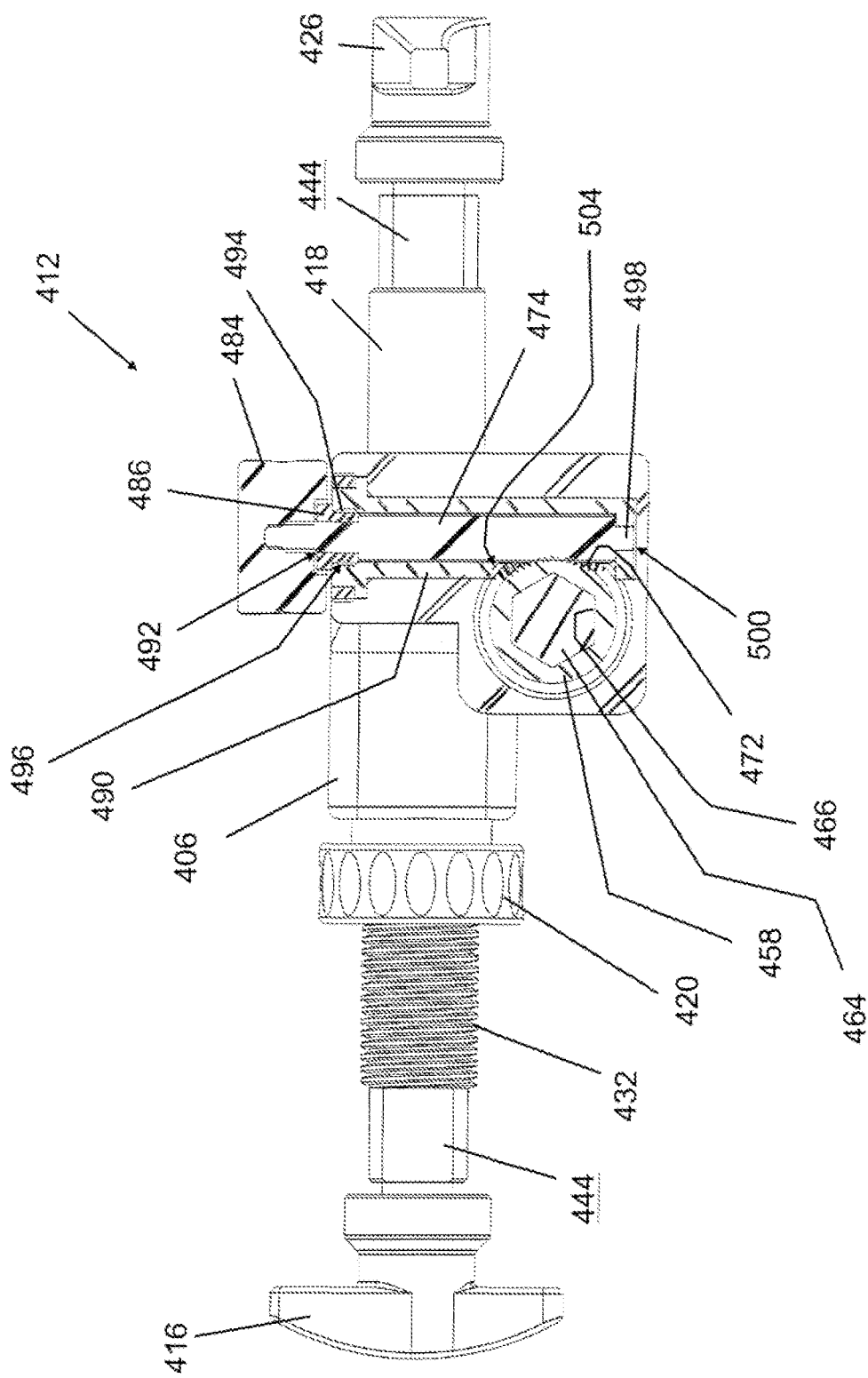
FIG. 12 depicts a cross section view taken along line 12-12 shown in FIG. 5.

FIG. 5 illustrates micro manipulator (400). Micro manipulator (400) comprises first assembly (402) and second assembly (404). First assembly (402) comprises body (406), first linear adjustment assembly (408), second linear adjustment assembly (410), and first angular adjustment assembly (412). As shown by comparing the views shown in FIGS. 8 and 9, first linear adjustment assembly (408) is configured to move body (406) linearly along axis (A4) as shown in FIG. 8. Second linear adjustment assembly (410) is configured to move body (406) along axis (A5) as shown in FIG. 8. First angular adjustment assembly (412) is configured to move second assembly (402) rotationally about axis (A5) as shown in FIG. 12. Additionally micro manipulator (400) includes a second angular adjustment assembly (414) on second assembly (404).

Figure 6B:
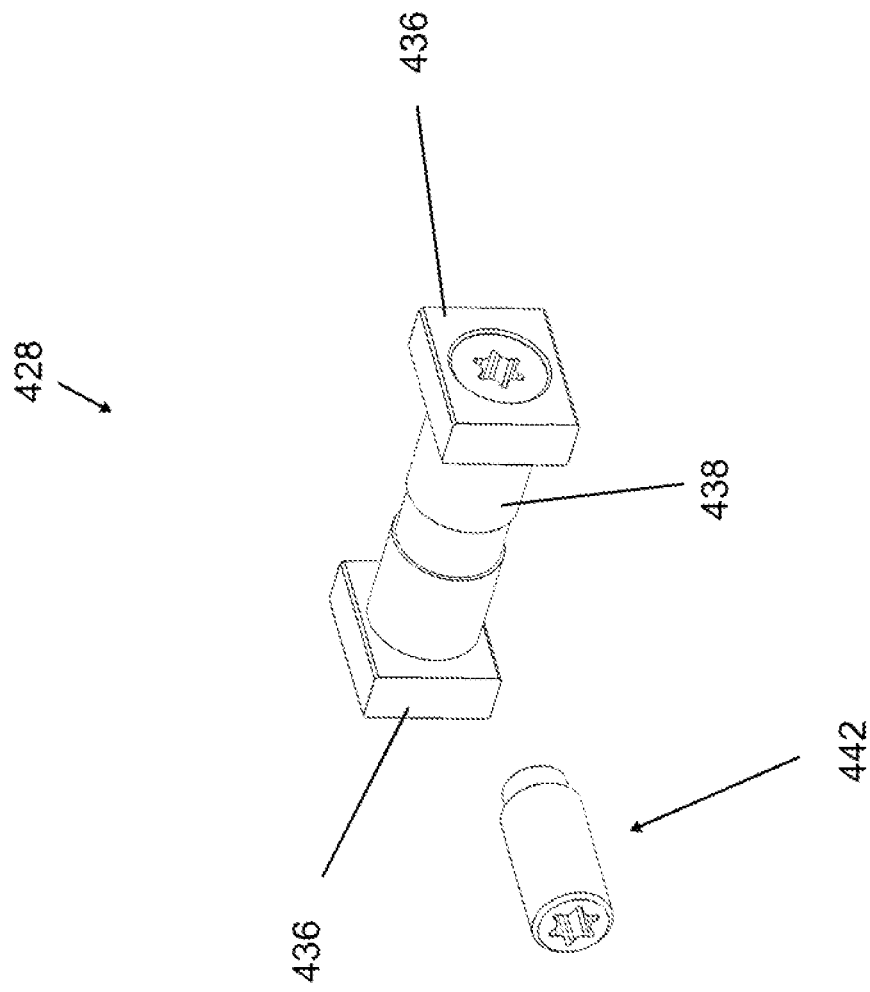
FIG. 6B depicts a perspective view an exemplary guide assembly used with the micro manipulator.

Referring to FIGS. 5-6B, first linear adjustment assembly (408) comprises first actuator (416), rod (418), insert (417), wheel (420), first ring (422), nut (423), second ring (424), second actuator (426), and guide assembly (428). Actuators (416, 426) threadably engage to the ends of rod (418). Furthermore, flat surfaces (444) of rod (418) are configured to be received within slots (252, 352) of positioning members (210, 310). Actuators (416, 426) can then be tightened to contact positioning members (210, 310) such that positioning members (210, 310) are secured with rod (418).

Referring now also to FIG. 7A, body (406) comprises bore (430) through which rod (418) extends. Rod (418) comprises threaded portion (432), and threaded portion (432) engages threaded bore (434) of insert (417) and also first threaded inner surface (429) of wheel (420). Insert (417) includes threaded outer surface (419) that engages second threaded inner surface (421) of wheel (420). Once insert (417) is threadably engaged with wheel (420), set screws are used to secure the relative position of insert (417) to wheel (420).

Rod (418) further comprises guide assembly (428) as shown in FIGS. 6A and 6B. Guide assembly (428) includes guides (436) that are received on post (438) once post (428) is extended through a bore in rod (418). Each of guides (436) is received within respective slots (440) of body (406). With guides (436) connected with post (428) and within slots (440), rod (418) is unable to rotate. Thus, with rotation of wheel (420), wheel (420) translates linearly along threaded portion (432) of rod (418) thereby providing a linear adjustment. Guide assembly (428) further includes set screw (442). Post (438) is configured to be out-of-round or not perfectly cylindrical such that the profile of a cross section across a transverse or latitudinal axis is not a perfect circle but instead more oval in shape. Furthermore, post (438) can be accessed from bore (441) of body (406) for rotational adjustment using a tool shaped to fit the end of post (438). With the shape of post (438), rotating post (438) moves guides (436) up or down within slots (440) depending on the direction of rotation. This forces guides (436) to contact either the upper or lower side of slots (440) in a snug fashion such that any play or freedom of movement of guides (436) within slot (440) is eliminated. Set screw (442) then securely holds post (438) in position, once adjusted as desired, by contacting or engaging a recessed region of post (438) to eliminate any play or freedom of movement between guides (436) and slots (440). Therefore, first linear adjustment assembly (408) includes features that allow linear adjustment along a first axis or in a first direction while minimizing or eliminating play or freedom of movement in other directions, i.e. perpendicular to the axis for linear adjustment.

Rings (422, 424) connect with openings of bore (430) in body (406) such that rings (422, 424) remain secured and stationary with respect to body (406). In the present example, rings (422, 424) have threaded outer surfaces (425, 427) that engage with threaded inner surfaces (431) of bore (430) of body (406). An end (433) of wheel (420) extends through ring (422) and within body (406). With this configuration wheel (420) (and connected insert (417)) remain able to rotate about the axis defined by rod (418) (axis A4). At the same time, assembled wheel (420) and insert (417) maintain their relative position with ring (422) because nut (423), positioned within body (406), threadably engages end (433) of wheel (420) thereby holding wheel (420) in place next to ring (422). As shown in the cross section view, wheel (420) includes a shoulder that contacts an outer surface of ring (422) when assembled. As will be apparent from the description above, end (433) of wheel (420) includes a threaded outer surface, and nut (423) includes a threaded inner surface that threadably engages the threaded outer surface of end (433) of wheel (420) as described above.

As wheel (420) (and connected insert (417) and nut (423) along with wheel (420)) is rotated, wheel (420) (and connected insert (417) and nut (423)) translate along threaded portion (432) of rod (418). Ring (422) and body (406) do not rotate but translate with wheel (420). In this motion, slots (440) of body (406) translate along guides (436) of rod (418). With this configuration, body (406) is able to be adjusted linearly in, for example, the X-direction along axis (A4). Furthermore, the translation of body (406) can be accomplished in either direction along axis (A4) depending on which way wheel (420) is rotated.

With the configuration described above, the amount of play between wheel (420) and rod (418) can be adjusted. The term "play" in this sense shall be understood to mean freedom of movement or space for movement. In some instances, if desired, the play can be nearly or completely eliminated. When the play is eliminated, any rotation of wheel (420) will produce translation of body (406). At the same time, body (406) has no freedom of movement when wheel (406) is stationary. In an example with play remaining in the system, body (406) has some freedom of movement even when wheel (420) is stationary. For instance, there may be small spaces between the threads of the engaged threaded portions, e.g. between the threads of wheel (420) that engage with the threads of rod (418). Such spaces may exist due to the degree of tolerances permitted in manufacturing components.

To control the play between wheel (420) and rod (418), insert (417) is loosened or tightened with respect to its threaded engagement with wheel (420). For example, to reduce or eliminate play in the system here, insert (417) is tightened with respect to wheel (420) by threadably engaging insert (417) with wheel (420) to a point where insert (417) places a force on wheel (420) directed toward body (406). With rod (418) stationary, this force on wheel (420) effectively moves the threads on wheel (420) that engage with the threads on rod (418) toward the side closest to body (406). Thus the threads of wheel (420) and rod (418) are contacting one another at the side closest to body (406) and any small space between the threads is now distributed to the opposite side furthest from body (406). Again, once inset (417) is set to the desired position based on the amount of desired play, set screws hold insert (417) in place such that the set desired amount of play is maintained.

Additionally, because insert (417) is also threadably engaged with rod (418), as insert (417) exerts force on wheel (420) by tightening insert (417) with respect to wheel (420), an opposite force is also exerted on insert (417) and such force is directed away from body (406). With rod (418) stationary, this force on insert (417) effectively moves the threads on insert (417) that engage with the threads on rod (418) toward the side furthest from body (406). Thus the threads of insert (417) and rod (418) are contacting one another at the side furthest from body (406) and any small space between the threads is now distributed to the opposite side closest to body (406).

Referring to FIGS. 5 and 7A-10, second linear adjustment assembly (410) comprises wheel (446), insert (447), rod (448), cap (450), first ring (452), nut (453), second ring (454), clip (456), and adapter (458). At one end of rod (448), cap (450) connects with rod (448). Rod (448) extends through insert (447), wheel (446), first ring (452), nut (453), bore (460) of body (406), adapter (458), second ring (454), and clip (456). Rod (448) comprises threaded portion (462) and hexagonal portion (464). Hexagonal portion (464) of rod (448) has a hexagonally shaped outer surface such that a cross section of rod (448) in the region of hexagonal portion (464) has a hexagon shape or profile. Adapter (458) and clip (456) comprise respective bores (466, 468) that have hexagonal openings configured to receive hexagonal portion (464). Insert (447) includes threaded bore (470) that is configured to threadably engage threaded portion (462) of rod (448). Wheel (446) includes bore with first threaded inner surface (471) that is also configured to threadably engage threaded portion (462) of rod (448). Insert (447) also includes threaded outer surface (445) that engages second threaded inner surface (473) of wheel (446). Once insert (447) is threadably engaged with wheel (446), set screws are used to secure the relative position of insert (447) to wheel (446). Adapter (458) is retained in place within body (406) by engagement of threaded portion (472) of adapter (458) with threaded rod (474) as shown in FIG. 12. With this configuration, rotation of wheel (446) does not cause rotation of rod (448). Instead, rotation of wheel (446) permits wheel (446) to translate along threaded portion (462) of rod (448).

Rings (452, 454) connect with openings of bore (460) in body (406) such that rings (452, 454) remain secured and stationary with respect to body (406). In the present example, rings (452, 454) have threaded outer surfaces (455, 457) that engage with threaded inner surfaces (459) of bore (460) of body (406). An end (461) of wheel (420) extends through ring (452) and within body (406). With this configuration wheel (446) (and connected insert (447)) remain able to rotate about the axis defined by rod (448) (axis A5). At the same time, assembled wheel (446) and insert (447) maintain their relative position with ring (452) because nut (453), positioned within body (406), threadably engages end (461) of wheel (446) thereby holding wheel (446) in place next to ring (452). As shown in the cross section view, wheel (446) includes a shoulder that contacts an outer surface of ring (452) when assembled.

As wheel (446) (and connected insert (447) and nut (453) along with wheel (446)) is rotated, wheel (446) (and connected insert (447) and nut (453)) translate along threaded portion (462) of rod (448). Ring (452) and body (406) do not rotate but translate with wheel (446). In this motion, adapter (458) is guided along hexagonal portion (464) of rod (448). With this configuration, body (406) is able to be adjusted linearly in, for example, the Y-direction along axis (A5). Furthermore, the translation of body (406) can be accomplished in either direction along axis (A5) depending on which way wheel (446) is rotated.

Figure 10:
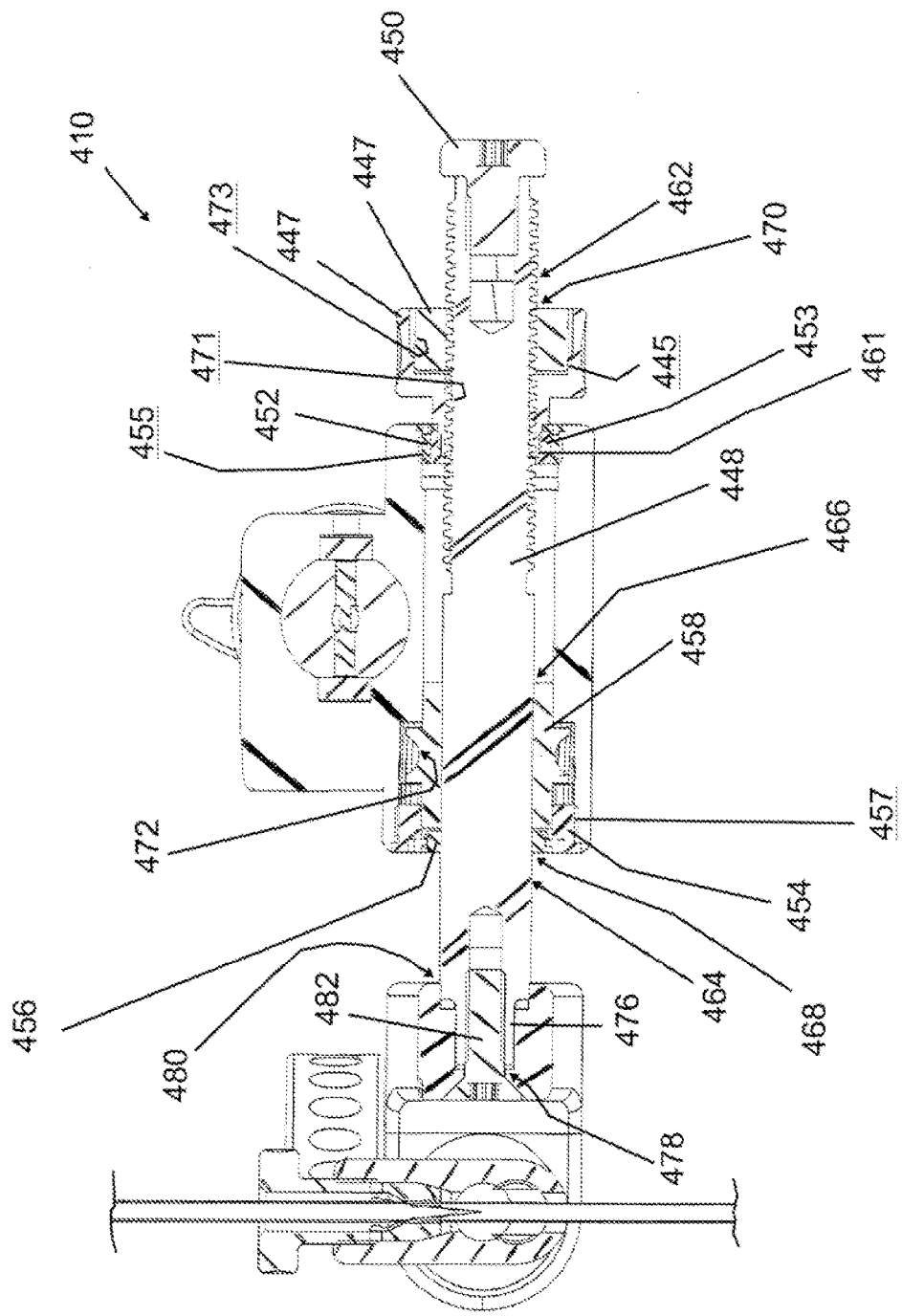
FIG. 10 depicts a cross section view taken along line 10-10 shown in FIG. 5.

Second linear adjustment assembly (410) connects with second assembly (404). Referring to FIG. 10, rod (448) comprises first end (476) having bore (478). First end (476) fits within bore (480) of second assembly (404) and screw (482) connects second assembly (404) with first end (476) by threadably engaging with bore (478). In this configuration, second assembly (404) is connected with first assembly (402).

With the configuration described above, the amount of play between wheel (446) and rod (448) can be adjusted. The term "play" in this sense shall be understood to mean freedom of movement or space for movement. In some instances, if desired, the play can be nearly or completely eliminated. When the play is eliminated, any rotation of wheel (446) will produce translation of body (406). At the same time, body (406) has no freedom of movement when wheel (446) is stationary. In an example with play remaining in the system, body (406) has some freedom of movement even when wheel (446) is stationary. For instance, there may be small spaces between the threads of the engaged threaded portions, e.g. between the threads of wheel (446) that engage with the threads of rod (448). Such spaces may exist due to the degree of tolerances permitted in manufacturing components.

To control the play between wheel (446) and rod (448), insert (447) is loosened or tightened with respect to its threaded engagement with wheel (446). For example, to reduce or eliminate play in the system here, insert (447) is tightened with respect to wheel (446) by threadably engaging insert (447) with wheel (446) to a point where insert (447) places a force on wheel (446) directed toward body (406). With rod (448) stationary, this force on wheel (446) effectively moves the threads on wheel (446) that engage with the threads on rod (448) toward the side closest to body (406). Thus the threads of wheel (446) and rod (448) are contacting one another at the side closest to body (406) and any small space between the threads is now distributed to the opposite side furthest from body (406). Again, once inset (447) is set to the desired position based on the amount of desired play, set screws hold insert (447) in place such that the set desired amount of play is maintained.

Additionally, because insert (447) is also threadably engaged with rod (448), as insert (447) exerts force on wheel (446) by tightening insert (447) with respect to wheel (446), an opposite force is also exerted on insert (447) and such force is directed away from body (406). With rod (448) stationary, this force on insert (447) effectively moves the threads on insert (447) that engage with the threads on rod (448) toward the side furthest from body (406). Thus the threads of insert (447) and rod (448) are contacting one another at the side furthest from body (406) and any small space between the threads is now distributed to the opposite side closest to body (406).

Figure 11:
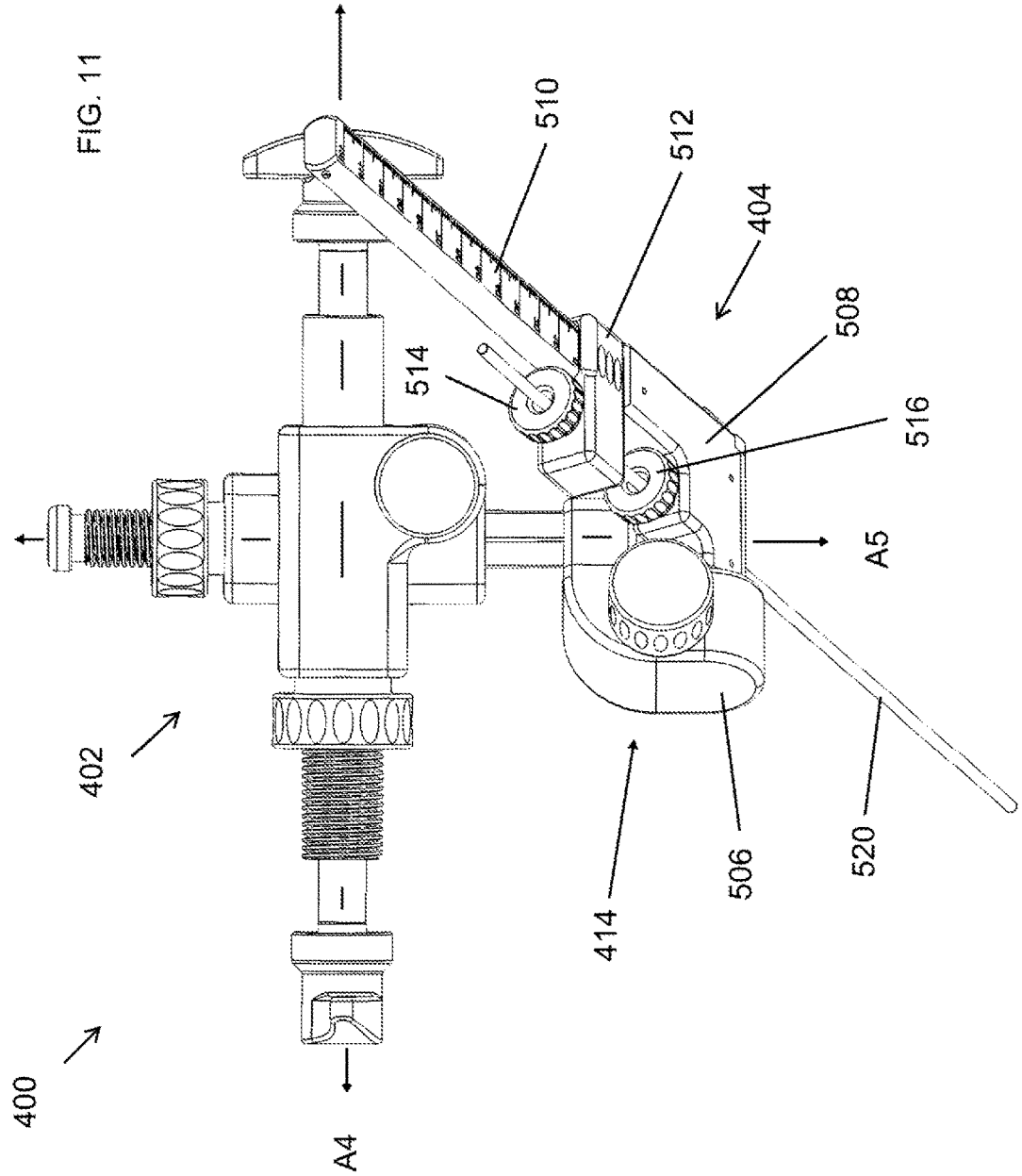
FIG. 11 depicts a top view of the micro manipulator as shown in FIG. 5, shown in a third adjustable position to show angular adjustments.

Referring to FIGS. 5, 11, and 12, first angular adjustment assembly (412) comprises wheel (484), threaded rod (474), nut (486), screws, guide (490), and adapter (458). Wheel (484), threaded rod (474), and screws connect such that rotation of wheel (484) produces a corresponding rotation of threaded rod (474). Nut (486) includes bore (492) and threaded rod (474) extends through bore (492). Nut (486) also includes threaded portion (494) that threadably engages threaded bore (496) of guide (490). When assembled, nut (486) holds threaded rod (474) in position relative to guide (490). Also threaded rod (474) has tip (498) that fits within bore (500) of guide (490).

Guide (490) is configured to fit within bore (502) of body (406) such that guide (490) does not move or change its position relative to body (406). Guide (490) further has a cut-out portion (504). Bore (502) of body (406) partially intersects bore (460) of body (406) within a region of body (406). When first angular adjustment assembly (412) is fully assembled, guide (490) fits within body (406) such that cut-out portion (504) aligns with the intersection of bore (502) of body (406) and bore (460) of body (406). Threaded rod (474) therefore also extends within the intersection of bores (502, 460). Moreover, threaded rod (474) aligns with adapter (458), and specifically threaded portion (472) of adapter (458). In the present example, threaded portion (472) of adapter (458) is configured with the threads or teeth circulating fully around adapter (458). Also, threaded rod (474) has threads that circulate fully around threaded rod (474). In this configuration adapter (458) can be rotated 360 degrees if desired.

In operating first angular adjustment assembly (412), wheel (484) is rotated. This rotation causes corresponding rotation in threaded rod (474). The engagement of the threads on threaded rod (474) with the threads on threaded portion (472) of adapter (458) causes adapter (458) to rotate in response to rotation of wheel (484) and threaded rod (474). The interference created by the hexagonal shape of bore (466) of adapter (458) with hexagonal portion (464) of rod (448) causes rod (448) to rotate in unison with rotation of adapter (458). Therefore rotation of wheel (484) produces rotation of rod (448). Since rod (448) is securely connected with second assembly (404) as described above, rotation of rod (448) causes corresponding rotation of second assembly (404). With this configuration then, first angular adjustment assembly is configured to rotate second assembly (404) about an axis defined by rod (448), which is illustrated as axis (A5). FIG. 11 illustrates such an exemplary rotation of second assembly (404).

Referring to FIGS. 5, 11, and 13-15, second assembly (404) comprises second angular adjustment assembly (414), first body (506), second body (508), scale bar (510), measurement member (512), first sleeve (514), second sleeve (516), stop pin (518), and instrument (520). Second angular adjustment assembly (414) comprises wheel (522), threaded rod (524), nut (526), screws (528), guide (530), and adapter (532). Wheel (522), threaded rod (524), and screws (528) connect such that rotation of wheel (522) produces a corresponding rotation of threaded rod (524). Nut (526) includes bore (534) and threaded rod (524) extends through bore (534). Nut (526) also includes threaded portion (536) that threadably engages threaded bore (538) of guide (530). When assembled, nut (526) holds threaded rod (524) in position relative to guide (530). Also threaded rod (524) has tip (540) that fits within bore (542) of guide (530).

Guide (530) is configured to fit within bore (544) of body (506) such that guide (530) does not move or change its position relative to body (506). Guide (530) further has a cut-out portion (546). Bore (544) of body (506) partially intersects bore (548) of body (506) within a region of body (506). When second angular adjustment assembly (414) is fully assembled, guide (530) fits within body (506) such that cut-out portion (546) aligns with the intersection of bore (544) of body (506) and bore (548) of body (506). Threaded rod (524) therefore also extends within the intersection of bores (544, 448). Moreover, threaded rod (524) aligns with adapter (532), and specifically threaded portion (550) of adapter (532). In the present example, threaded portion (550) of adapter (532) is configured with the threads or teeth circulating fully around adapter (532). Also, threaded rod (524) has threads that circulate fully around threaded rod (524). In this configuration adapter (532) could be rotated 360 degrees if desired, although rotation may be limited by at least some extent due to interference of second assembly (404) with first assembly (402).

In operating second angular adjustment assembly (414), wheel (522) is rotated. This rotation causes corresponding rotation in threaded rod (524). The engagement of the threads on threaded rod (524) with the threads on threaded portion (550) of adapter (532) causes adapter (532) to rotate in response to rotation of wheel (522) and threaded rod (524). Furthermore, adapter (532) comprises threaded portion (552) that engages with threaded bore (554) of second body (508). Pin (556) secures second body (508) with threaded portion (552) of adapter (532). This connection causes second body (508) to rotate in unison with rotation of adapter (532). Therefore rotation of wheel (522) produces rotation of second body (508) about an axis defined by second body (508), which is illustrated as axis (A6) in FIG. 8. FIG. 11 further illustrates such an exemplary rotation of second body (508).

FIG. 14 illustrates a cross section view taken along axis (A6). As shown, stop pin (518) extends within second body (508) and is held in place by pin (558), which is received within groove (560) of stop pin (518). In this arrangement, stop pin (518) can rotate in place without translating relative to second body (508). Stop pin (518) comprises slot (562) at one end and tab (564) at the opposing end. Tab (564) is available for a user to grasp for rotating stop pin (518). Slot (562) is defined by wings (566). Second body (508) comprises opening (568) at its underside. When stop pin (518) is in a first position as shown in FIG. 14, wings (566) do not obstruct or block opening (568) such that instrument (520) can extend through opening (568). However, stop pin (518) can be rotated when instrument (520) is not yet extending through opening (568) to thereby block or close opening (568) such that instrument (520) is prevented from extending through opening (568).

Figure 16:
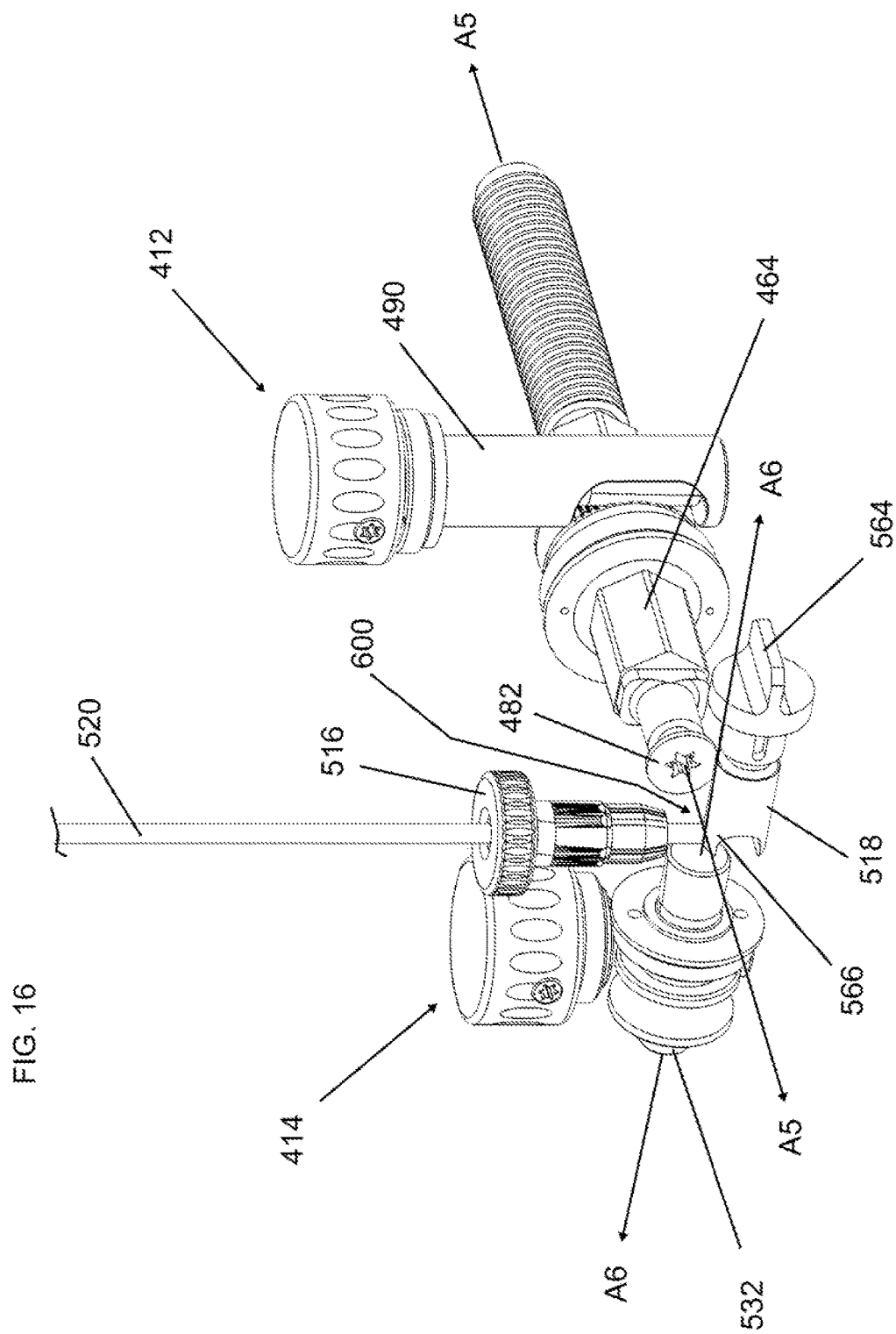
FIG. 16 depicts a partial view of certain components of the first and second angular adjustment assemblies of the micro manipulator shown in FIG. 5.

Referring to FIG. 16, first and second angular adjustment assemblies (412, 414) are shown without bodies (406, 506, and 508) to show alignment of internal components. Furthermore, stop pin (518) is shown rotated to the closed position. When stop pin (518) is closed to bock or close opening (568), instrument (520) can be positioned within micro manipulator (400) such that it rests upon or contacts the upper wing (566) of stop pin (518). In the present example, when instrument (520) is in this position the navigation point (600), also referred to as the tip or end of the instrument in some instances, is positioned at the intersection of the rotational axes, e.g., at the intersection of axes A5 and A6. With this configuration, rotational adjustment of instrument (520) can be made about one of the rotational axes without displacing navigation point (600) from the other of the rotational axes, and vice versa. For example, referring to FIG. 8, first angular adjustment assembly (412) can be actuated to rotate second assembly (404) counter-clockwise about axis A5. With stop pin (518) closed such that instrument (520) contacts upper wing (566) of stop pin (518), navigation point (600) remains at the intersection of axes A5 and A6. The same is true where second angular adjustment assembly (414) is actuated to rotate body (508) of second assembly (404) relative to body (506) of second assembly (404); that is navigation point (600) remains at the intersection of axes A5 and A6 despite the rotational adjustment.

Moreover, if the instrument tip or navigation point (600) does not fall upon, intersect, or otherwise remain in-line with the two rotational axes as mentioned above, then a rotation of micro manipulator (400) about one of the rotational axes would lead to a displacement of tip (600) in a linear manner. In such an instance, one would need to adjust micro manipulator (400) along at least one of the linear axes, A4 and/or A5, to position tip (600) of instrument (520) at the same position relative to the position of tip (600) prior to the rotational adjustment. In other words, instrument (520) can have a first and second angle or trajectory based on rotational adjustments made to micro manipulator (400). And with the configuration described above where tip (600) of instrument (520) intersects or is otherwise in-line with the rotational axes A5 and A6, it is possible to avoid linear displacement of tip (600) of instrument (520) when making a rotational adjustment of micro manipulator (400) to reposition instrument (520) from the first angle or trajectory to the second angle or trajectory. Thus, micro manipulator (400) is configured with one or more features that permit navigation point or tip (600) to be positionable at the intersection of at least two rotational axes, and remain at the intersection during rotational adjustment without displacing the navigation point or tip (600) in a linear manner. This configuration thus allows for a trajectory adjustment without necessarily altering a desired target, which could be an insertion or entry point on the patient.

Sleeves (514, 516) are configured to selectively retain instrument (520). For instance, when first inserting instrument (520) within sleeves (514, 516), sleeves (514, 516) allow instrument to extend through sleeves (514, 516). Sleeves (514, 516) can then be tightened such that they securely grasp instrument (520) such that instrument (520) can move in unison with sleeves (514, 516) but not relative to sleeves (514, 516). Furthermore, sleeves (514, 516) can be tightened and loosened independent from one another such that instrument (520) may be able to move relative to one of sleeves (514, 516), but may only move in unison with the other of sleeves (514, 516).

Instruments (520) for use with system (10) include, but are not limited to, biopsy devices, endoscopes, needles, drills, electrodes, seeds, among others. Micro manipulator (400) serves as a guide and positioning system for these and other instruments. For example, measurement member (512) and scale bar (510) provide a user with a guide for measuring and setting a desired depth of penetration for instrument (520). At the same time, the linear and angular adjustability provided by first linear adjustment assembly (408), second linear adjustment assembly (410), first angular adjustment assembly (412), and second angular adjustment assembly (414) provide a user with a precise positioning system such that a desired placement and angle or trajectory can be achieved with instrument (520). Also, by unlocking articulated arms (200, 300) further positioning of micro manipulator (400) is achieved. In some instances, adjustment using articulated arms (200, 300) is considered a coarse adjustment such that articulated arms (200, 300) are considered a coarse adjustment means, while adjustment using first linear adjustment assembly (408), second linear adjustment assembly (410), first angular adjustment assembly (412), and second angular adjustment assembly (414) is considered a fine adjustment such that each of first linear adjustment assembly (408), second linear adjustment assembly (410), first angular adjustment assembly (412), and second angular adjustment assembly (414) are considered a fine adjustment means.

In some instances, system (10) or components of system (10) are used in navigated stereotaxy or stereotactic procedures. In such procedures, instrument (520) and/or micromanipulator (400) communicates with a navigation system. For instance, exemplary navigation systems can include, those commercially available from Medtronic Inc., Brainlab AG, and Stryker. In such example procedures, a surgeon or user has a planned entry point on the patient, trajectory for inserting instrument (520) at the entry point, and target point within the patient. These planned points or coordinates are transferred to the navigation system. Instrument (520), which again may communicate with the navigation system, can be positioned while at the same time checking or verifying the position with the navigation system.

Figure 15:
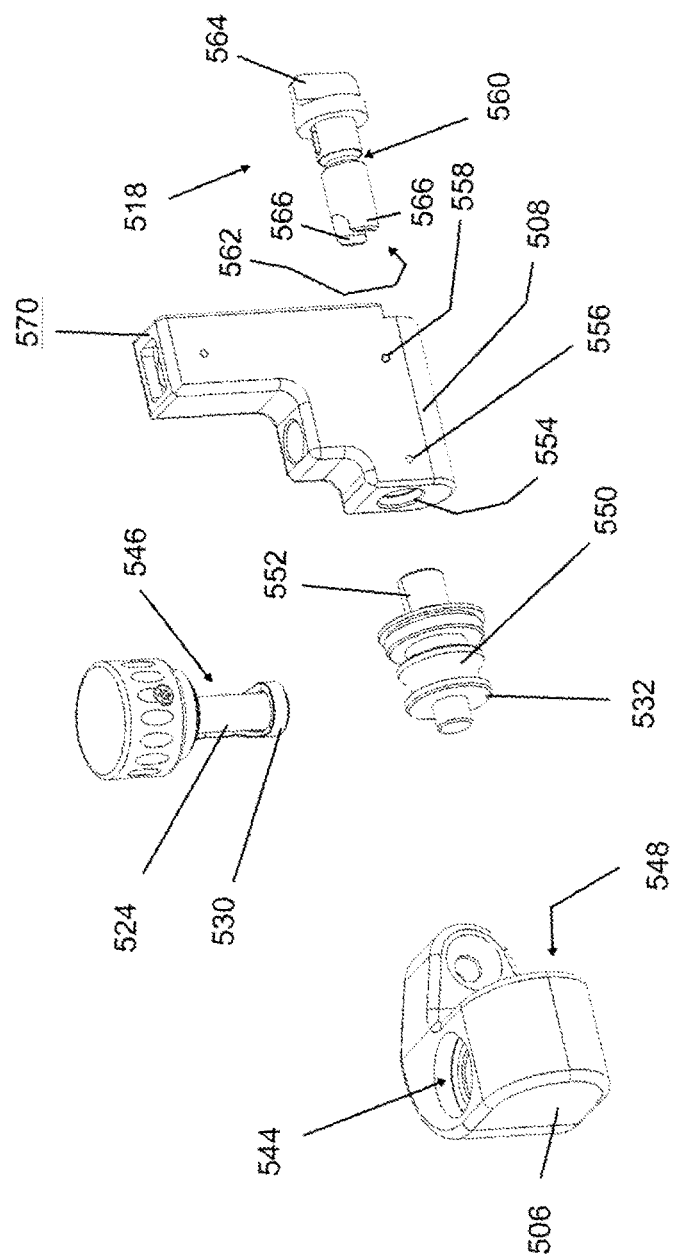
FIG. 15 depicts a partially exploded view of a portion of the micro manipulator as shown in FIG. 5.

In an exemplary procedure, exemplary steps for positioning instrument (520) can begin with making gross adjustments via adjusting articulated arms (200, 300). Next, fine angular adjustments can be made using first and second angular adjustment assemblies (412, 414). Next, fine linear adjustments can be made using first and second linear adjustment assemblies (408, 410). Next, micro manipulator (400) can be removed temporarily form articulated arms (200, 300) while a surgeon or user creates an opening at the desired entry point, for example via drilling, cutting, etc. In some instances, removing micro manipulator (400) is not necessary to create the opening at the desired entry point. For instance, an entry point might already exist, or a drill may be configured to removably fit through sleeves of micro manipulator (400) to create the entry point. In instances when micro manipulator (400) is removed from arms (200, 300) to create the opening or for another reason, micro manipulator (400) can then be reconnected with articulated arms (200, 300) to the same position it previously had or maintained, without the need to repeat prior positioning adjustments made to micro manipulator (400). Next, with micro manipulator (400) back in position and secured in articulated arms (200, 300), instrument (520) is positioned within sleeves (514, 516) and measurement member (512) adjusted along scale bar (510) to correspond to a desired penetration depth. Next, instrument (520) is inserted at the entry point with sleeve (514) securely holding instrument (520) while sleeve (516) is loosened such that instrument (520) is free to pass through sleeve (516). Measurement member (512) is then advanced downward along scale bar (510) toward the entry point on the patient until measurement member (512) contacts an upper surface (570) of second body (508), for example as shown in FIGS. 14-15. Other methods or modifications of the exemplary methods herein will be apparent to those of ordinary skill in the art in view of the teachings herein.

In some versions, the exemplary components shown and described herein are made of plastic or other radiolucent materials such that system (10) or components thereof can be used with various imagining modalities. In such instances, it would not be necessary to remove system (10) or components thereof prior to imagining a patient. Of course in other versions system (10) and/or components thereof may be made of other materials that will be apparent to those of ordinary skill in the art in view of the teachings herein.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A device for positioning a surgical instrument, the device comprising:
    (a) a first adjustment assembly having a first actuator to adjust the device linearly along a first axis;
    (b) a second adjustment assembly having a second actuator to adjust the device linearly along a second axis;
    (c) a third adjustment assembly having a third actuator to adjust the device rotationally;
    (d) a fourth adjustment assembly having a fourth actuator to adjust the device rotationally; and
    (e) wherein each of the first, second, third, and fourth adjustment assemblies are actuated by rotating about separate axes of rotation.

2. The device of claim 1 wherein the first, second, third, and fourth adjustment assemblies provide fine adjustment.

3. The device of claim 2 further comprising an attachment member selectively connectable with an adjustable arm.

4. The device of claim 3 wherein the adjustable arm provides coarse adjustment of the device.

5. The device of claim 1 wherein the first, second, third, and fourth adjustment assemblies adjust the device such that each adjustment is independent from each other adjustment.

6. The device of claim 1 wherein the first axis and the second axis are perpendicular.

7. The device of claim 1 wherein the third adjustment assembly adjusts the device rotationally about the second axis.

8. The device of claim 1 wherein the fourth adjustment assembly adjusts the device rotationally about a third axis.

9. The device of claim 8 wherein the second axis and the third axis are perpendicular.

10. The device of claim 8 further comprising a stop feature that maintains a navigation point of the surgical instrument along the second axis and along the third axis when the stop feature is in a closed position.

11. The device of claim 10 wherein the stop feature maintains the navigation point of the surgical instrument at an intersection of the second axis and the third axis when the stop feature is in the closed position.

12. The device of claim 1 further comprising a first rotational axis about which the third adjustment assembly adjusts the device and a second rotational axis about which the fourth adjustment assembly adjusts the device, wherein the second rotational axis intersects the first rotational axis.

13. A device for positioning a surgical instrument, the device comprising:
   (a) a first adjustment assembly having a first actuator to adjust the device linearly along a first axis;
   (b) a second adjustment assembly having a second actuator to adjust the device linearly along a second axis;
   (c) a third adjustment assembly having a third actuator to adjust the device rotationally;
   (d) a fourth adjustment assembly having a fourth actuator to adjust the device rotationally;
   (e) a first rotational axis about which the third adjustment assembly adjusts the device;
   (f) a second rotational axis about which the fourth adjustment assembly adjusts the device, wherein the second rotational axis intersects the first rotational axis; and
   (g) a stop feature that maintains a tip of the surgical instrument at an intersection of the first and second rotational axes when the stop feature is in a closed position.

14. The device of claim 13 wherein the tip of the surgical instrument is maintained at the intersection of the first and second rotational axes when the device is rotationally adjusted about a select one of the first and the second rotational axes.

15. A device for positioning a surgical instrument, the device comprising:
   (a) a first adjustment assembly having a first actuator to adjust the device linearly along a first axis;
   (b) a second adjustment assembly having a second actuator to adjust the device linearly along a second axis;
   (c) a third adjustment assembly having a third actuator to adjust the device rotationally;
   (d) a fourth adjustment assembly having a fourth actuator to adjust the device rotationally; and
   (e) wherein each of the first and second adjustment assemblies comprise an adjustment to control the amount of free movement within each of the first and second adjustment assemblies.

* * * * *